US00RE36273E

United States Patent [19]

Brannon

[11] E Patent Number: Re. 36,273

[45] Reissued Date of Patent: Aug. 17, 1999

[54] SYRINGE APPARATUS FOR SEPARATING BLOOD

[75] Inventor: James K. Brannon, Culver City, Calif.

[73] Assignee: Vascular Logics, Inc., Huntington Beach, Calif.

[21] Appl. No.: 08/967,556

[22] Filed: Nov. 12, 1997

Related U.S. Patent Documents

Reissue of:

[64] Patent No.: 5,518,005
Issued: May 21, 1996
Appl. No.: 08/426,702
Filed: Apr. 24, 1995

[51] Int. Cl.[6] ..... A61B 5/00

[52] U.S. Cl. ..... 600/578; 604/231

[58] Field of Search ..... 600/573, 576–579; 604/184, 187, 192, 205, 231

[56] References Cited

U.S. PATENT DOCUMENTS

| | | | |
|---|---|---|---|
| 701,671 | 6/1902 | Billings . | |
| 1,272,742 | 7/1918 | Weguelin et al. . | |
| 1,410,530 | 3/1922 | Laraché . | |
| 3,931,815 | 1/1976 | Takatsuki . | |
| 4,150,666 | 4/1979 | Brush . | |
| 4,274,408 | 6/1981 | Nimrod | 128/214.4 |
| 4,312,362 | 1/1982 | Kaufman | 128/763 |
| 4,378,812 | 4/1983 | Sarstedt | 128/756 |
| 4,660,569 | 4/1987 | Etherington | 128/765 |
| 4,936,315 | 6/1990 | Lineback | 128/765 |
| 5,045,065 | 9/1991 | Raulerson | 604/167 |
| 5,133,362 | 7/1992 | Moss | 128/763 |
| 5,147,329 | 9/1992 | Brannon | 604/231 |
| 5,324,266 | 6/1994 | Ambrisco et al. | 604/125 |
| 5,474,546 | 12/1995 | Ambrisco et al. | 604/411 |

FOREIGN PATENT DOCUMENTS

| | | |
|---|---|---|
| 3025800 A1 | 2/1982 | Germany . |
| WO 88/03778 | 6/1988 | WIPO . |

*Primary Examiner*—Max Hindenburg
*Attorney, Agent, or Firm*—Lyon & Lyon LLP

[57] ABSTRACT

A disposable syringe for the dual extraction of arterial blood or venous blood into the barrel of said disposable syringe and a plurality of vacuum glass tubes. The distal portion of the syringe has an inner cannula extending centrally retrograde from the distal portion of the syringe and telescoping into the proximal portion of a conduit of a plunger of the syringe with said plunger of the syringe having a piston which sealably slides lengthwise about said inner cannula and said conduit of said plunger further having one end thereof sealably accepting a blood collection needle of a blood collection receptacle with said inner cannula telescoping further centrally retrograde into said conduit of said plunger with the distal portion of said inner cannula being securely positioned into the distal portion of the syringe so as to allow arterial or venous blood to flow around said inner cannula and into the barrel of the syringe when said plunger is advanced proximally with said inner cannula inducing the flow of arterial or venous blood when a vacuum glass tube is inserted into said blood collection receptacle. Several embodiments of the inner cannula plunger-conduit system are described.

24 Claims, 7 Drawing Sheets

SYRINGE APPARATUS FOR SEPARATING BLOOD

Matter enclosed in heavy brackets [ ] appears in the original patent but forms no part of this reissue specification; matter printed in italics indicates the additions made by reissue.

BACKGROUND OF THE INVENTION

1. Field of the Invention

This invention relates to a syringe having an inner cannula integral with the distal portion of said syringe and a piston sealably engaging said inner cannula with said piston integral with a plunger-conduit system. The inner cannula is integral with the distal portion of the syringe and positioned therein so as to allow a fluid to flow around said inner cannula and into the barrel of the syringe when said piston is advanced proximally and in so doing, this first obtained fluid is separate from a second fluid which can be obtained by inserting a vacuum glass tube into a fluid collection receptacle attached to the plunger conduit system. After a plurality of vacuum tubes are filled with the second obtained fluid, the first obtained fluid can be returned to the patient by simply advancing the piston distally.

2. Information Disclosure Statement

Since the advent of the Acquired Immune Deficiency Syndrome (AIDS), many disposable devices have been developed to prevent accidental needle sticks. However, prior art lacks simplicity and blood drawing procedures found traditionally cumbersome are now made unusually complex. Yet even further, as cost containment becomes more important, the additional blood drawing components found in prior art touted as being safe are now realized to be unusually complex, not universally applicable, and consequently not cost worthy.

Often, severely ill patients in the hospital will require central venous catheterization for administration of various medicinal preparations and arterial catheterization for monitoring of blood pressure.

Regarding central venous catheterization, often a triple lumen catheter will be placed in the patient's subclavian vein and at least one lumen of the catheter is used for the administration of fluid; the two remaining unused lumens may be used to draw blood for laboratory testing or alternately the administration of a variety of other medicinal preparations. If a given lumen of the central venous catheter is used to obtain a blood sample for laboratory testing, a syringe is attached to the unused lumen and this first obtained venous blood considered too dilute for laboratory testing is drawn into the barrel of the syringe, the syringe is then detached and discarded. A second syringe is then attached to this lumen and a second obtained volume of venous blood is drawn into the barrel of the syringe. The volume of venous blood obtained is limited by the volume of the syringe. This second obtained venous blood is then transferred to vacuum glass tubes by cumbersome traditional methods.

Regarding arterial catheterization, an arterial catheter is inserted into the patient's radial artery. The now inserted arterial catheter can then be attached to a blood pressure monitor. The connection to the blood pressure monitor is established with pressure tubing having at least one three-way valve proximal to the catheter insertion site. When monitoring blood pressure, heparinized solution fills the pressure tubing to the level of the catheter insertion site distally and a pressure transducer proximally. In the monitoring mode, the three-way valve is patent with the distal catheter and the proximal pressure transducer. Simultaneously, the three-way valve is closed to a blood sampling side port used to obtain blood samples for laboratory testing. To obtain blood for laboratory testing, the three-way valve is closed toward the proximal pressure transducer and patent toward the distal catheter and the blood sampling side port. Thereafter, a syringe is attached to the blood sampling side port and a first obtained volume of arterial blood considered too dilute for laboratory testing is drawn into the barrel of the syringe and the syringe is then detached. A second syringe is then attached to the blood sampling side port and a second obtained volume of arterial blood is drawn into the barrel of the syringe. This second obtained volume of arterial blood considered appropriate for laboratory testing is transferred to vacuum glass tubes in a traditional manner found to be cumbersome and unusually complex by those familiar with prior art. The three-way valve is then positioned to make patent the arterial catheter distally and the pressure transducer proximally so that the patient's blood pressure can be continuously monitored.

In view of the aforementioned cumbersome manipulations and unusually complex devices used to obtain a single sample of venous or arterial blood from an indwelling catheter, the objectives of the present invention are set forth and described herein.

In preparation for this application, a search was completed in Class 604, Subclass 231 and 187, Class 128, Subclass 214.4. In contradistinction to the patent application at hand U.S. Pat. No. 4,274,408 of Nimrod teaches a displaceable feeder tube contained within a syringe barrel having a function readily distinguishable from that which follows.

SUMMARY AND OBJECTS OF THE PRESENT INVENTION

It is an object of the present invention to provide an improved method for obtaining a plurality of blood samples for vacuum glass tubes from indwelling arterial or venous catheters from a single syringe apparatus.

It is an object of the present invention to provide means for separating a first obtained volume of blood considered too dilute for laboratory testing from a second obtained volume of blood considered appropriate for laboratory testing using a single syringe.

It is an object of the present invention to provide a single syringe apparatus that can be attached to an indwelling central venous catheter or an indwelling arterial catheter for purposes of obtaining a plurality of blood samples.

SUMMARY

The invention describes a syringe apparatus having an inner cannula positioned securely in the distal portion of said syringe apparatus so as to allow fluid to flow past the inner cannula and into the barrel of the syringe. This first obtained fluid considered too dilute for testing remains separate from a second obtained fluid which passes through the inner cannula, a plunger-conduit system and into a plurality of vacuum glass tubes inserted into a blood collection receptacle integral with the plunger-conduit system. The piston of the syringe apparatus sealably engages the inner cannula and slides lengthwise about the inner cannula when the plunger-conduit system is advanced in a proximal or distal direction. The outer-diameter of the inner cannula is smaller than the inner diameter of the plunger-conduit system and thereby facilitates telescoping of the inner cannula within the plunger-conduit system when the plunger conduit system is advanced in a proximal or distal direction while the piston of the syringe apparatus keeps separate a first obtained fluid considered too dilute for laboratory testing from a second obtained fluid considered appropriate for laboratory testing induced to pass through the inner cannula and the plunger-conduit system when a plurality of vacuum glass tubes are inserted into a blood collection receptacle integral with the plunger-conduit system.

DESCRIPTION OF THE PREFERRED EMBODIMENTS

Figure 1:
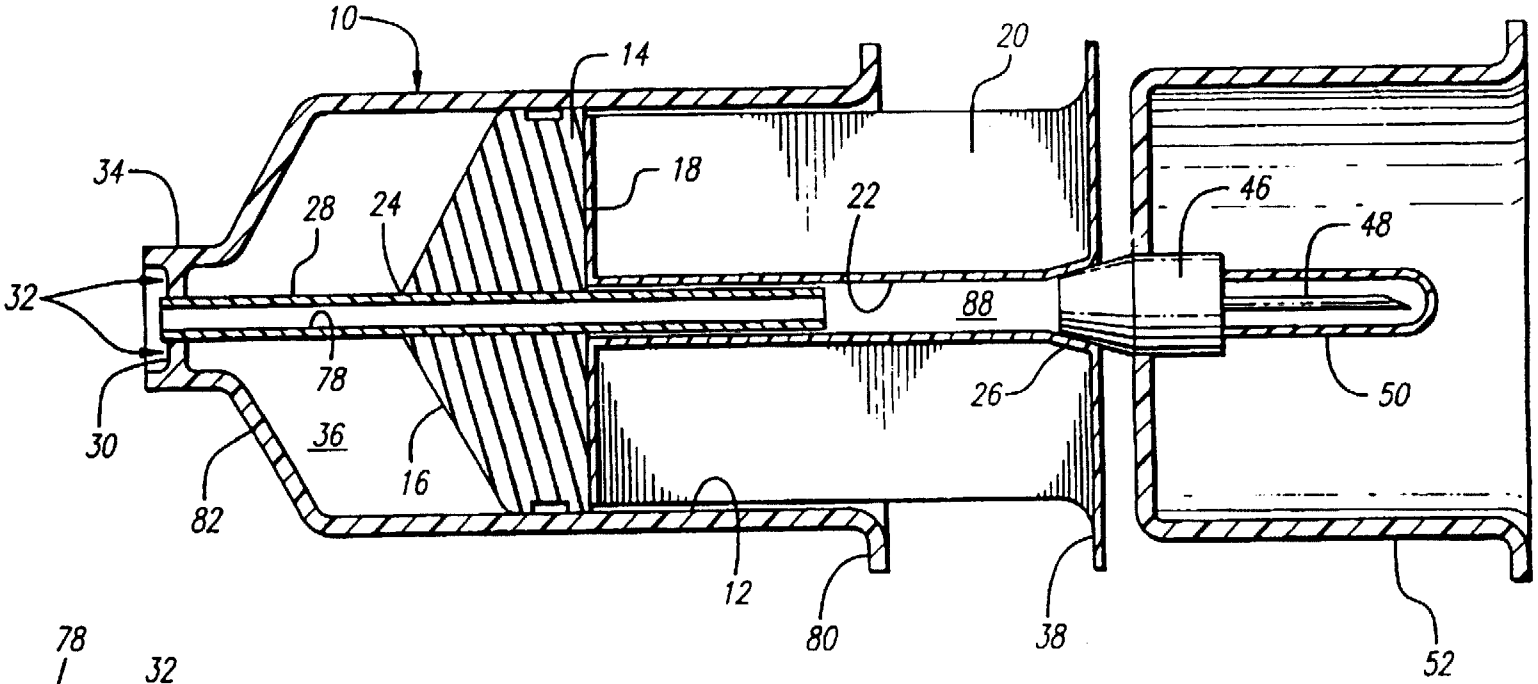
FIG. 1 is a sectional view of the syringe of the present invention with the piston thereof positioned proximally to show the inner cannula within the syringe tip distally and the plunger-conduit system proximally.

The apparatus of the present invention is exemplified by the embodiment of FIG. 1, which shows a syringe type device with a customary cylindrical body 10 terminating at an end wall 82 integral with a distal hub 34. Integral with the distal hub 34 is a supporting bar 30 which partially occludes a hub opening 32. The support bar 30 rigidly holds and prevents axial or lateral movement of an inner cannula 28. The inner cannula 28 has origin at the distal hub 34 and not beyond and extends proximally and not beyond a thumb rest 80 which is integral with the cylindrical body 10. The piston 14 is mounted to the plunger 20 at a piston mounting face 18 with the piston 14 having been fitted into the proximal end of the cylindrical body 10 to establish a fluid seal at the juncture thereof and the interior wall 12 of the cylindrical body 10. The piston 14 has a fluid-chamber face 16 which establishes a fluid chamber 36 through which the inner cannula 28 passes. The outer diameter of the inner cannula 28 is substantially larger than the inner diameter of the central opening 24 of the piston 14 so as to create a slidable fluid seal at the juncture thereof and the outer diameter of the inner cannula 28. The inner cannula 28 has a substantially narrow inner diameter defined by a smooth inner wall 78. The outer diameter of the inner cannula 28 is substantially smaller than the inner diameter of the conduit 22 so as to allow telescoping of the inner cannula 28 into the conduit 22 of the plunger 20 when the plunger is advanced in a proximal or distal direction. At the proximal end of the conduit 22 is a funnel shaped opening 26 to which a blunt blood collection needle 46 integral with a blood collection receptacle 52 is sealably mounted. Often, blunt blood collection needles of this variety have a proximal needle 48 housed within a rubber sleeve 50. The cooperative functional elements define the fluid chamber 36 which is substantially separate from a fluid chamber 88.

Figure 2:
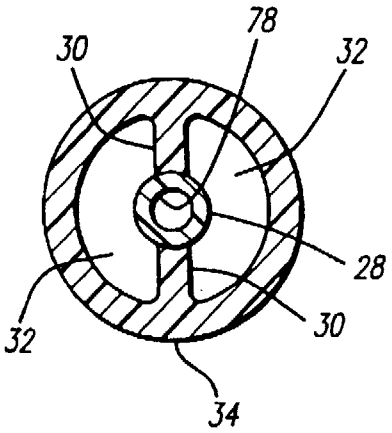
FIG. 2 is an exploded cross section view of the distal portion of the syringe of this invention.

The distal hub 34 is further exemplified in FIG. 2 to show the support bars 30 in cross section partially occluding the hub opening 32. The hub opening 32 freely communicates with the fluid chamber 36 as shown in FIG. 1.

Figure 3:
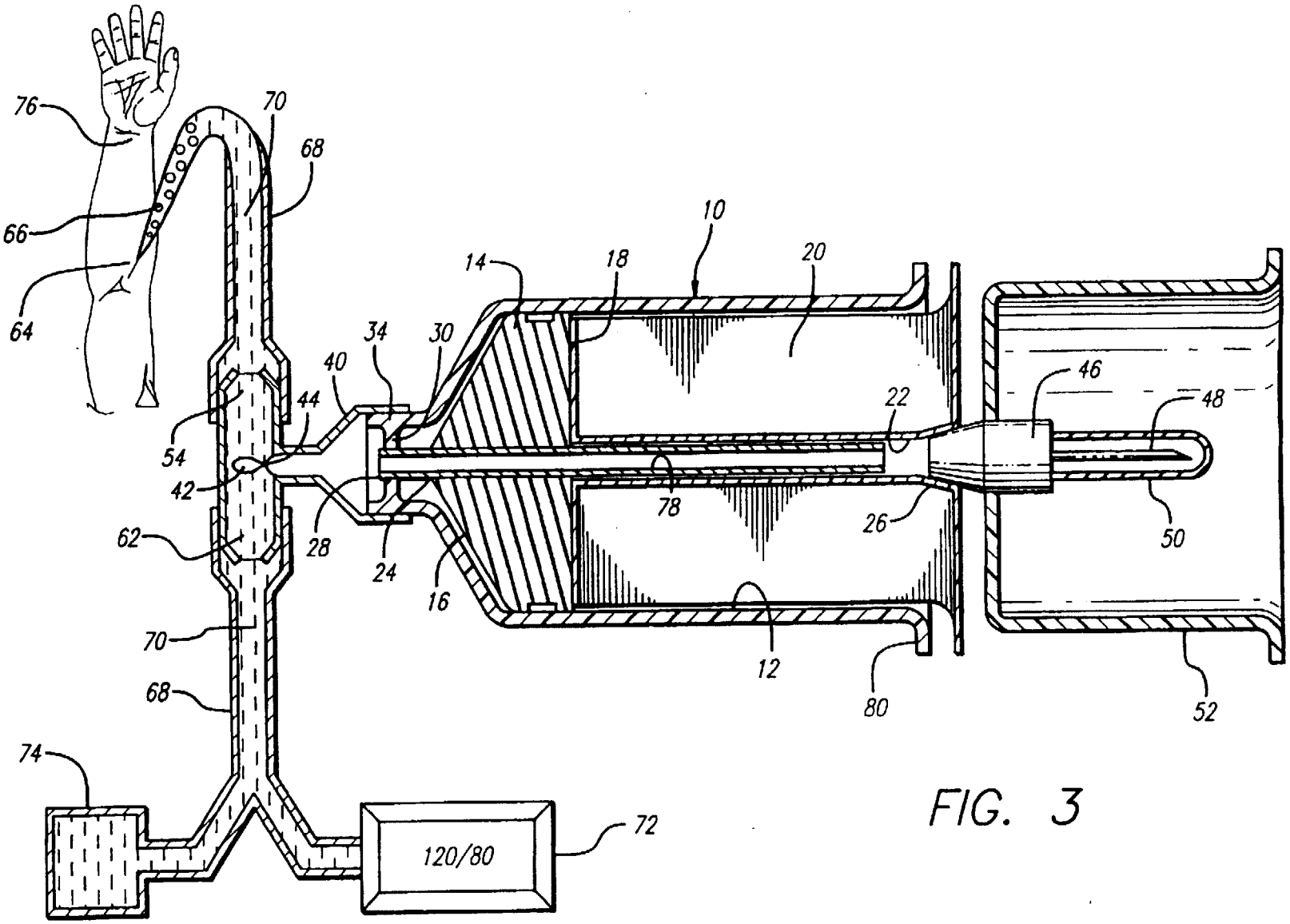
FIG. 3 is a sectional view of the syringe of the present invention attached to arterial pressure tubing at a side blood sampling port.

The functional and operative position of the syringe apparatus is shown in FIG. 3 wherein a blood sampling side port 40 is mounted to the distal hub 34. A three-way valve 42 having an off indicator tip 44 is integral with a distal port 54 and proximal port 62. In the operative position shown the distal port 54 and the proximal port 62 freely communicate. Integral with the distal port 54 is a transparent pressure tube 68 which is attached to a patient's radial artery 64 of a wrist 76. The pressure tube 68 contains a first obtained fluid 70 which is partially mixed with a second obtained fluid 66. Integral with the proximal port 62 is the transparent pressure tube 68 attached to a fluid reservoir 74 and a pressure transducer 72 with a blood pressure reading of 120/80.

Figure 4:
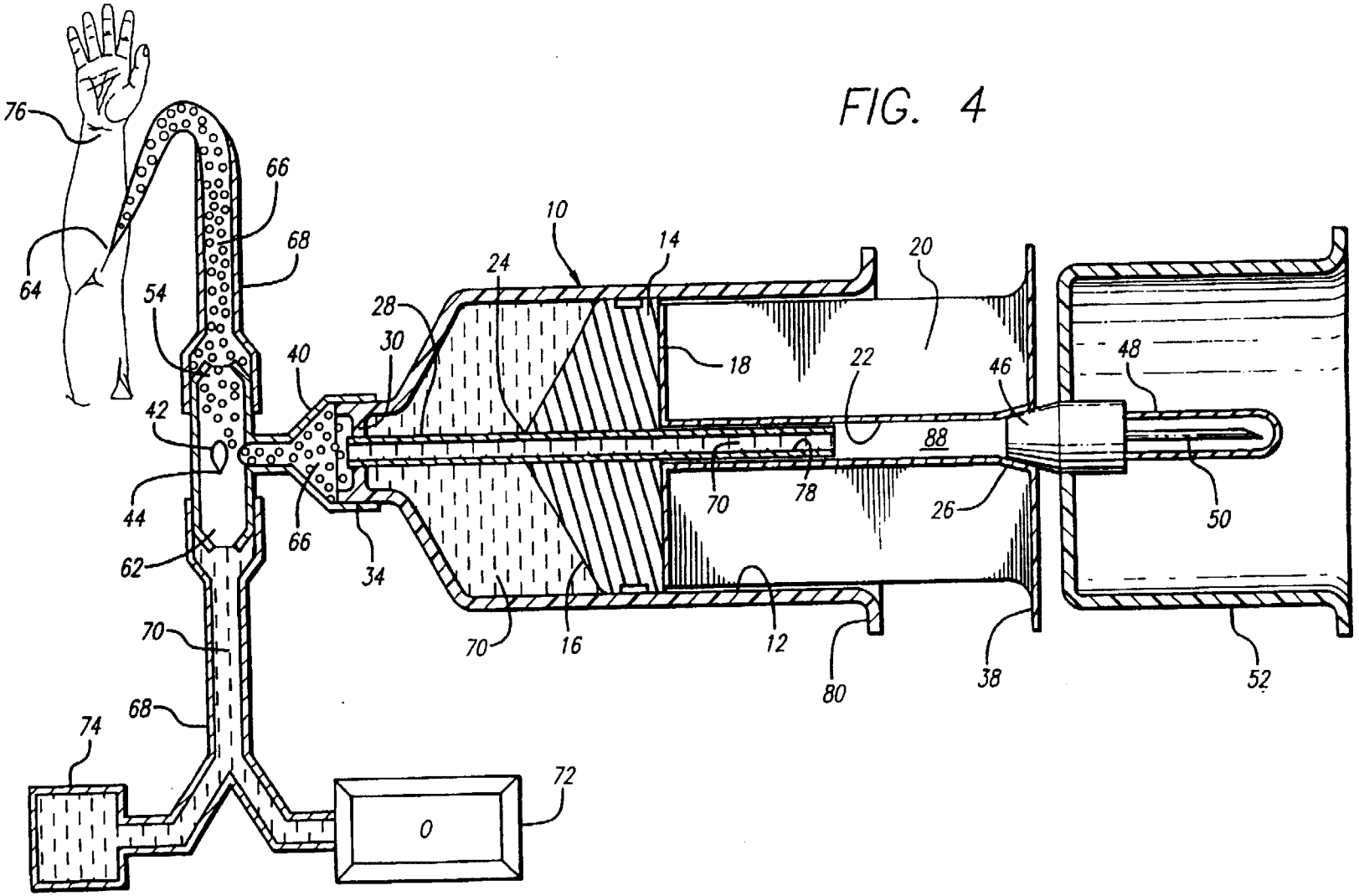
FIG. 4 is a sectional view of the syringe of the present invention with first obtained fluid within the barrel of the syringe.

FIG. 4 shows the three-way valve 42 with the off indicator tip 44 directed toward the proximal port 62 thereby allowing the distal port 54 to freely communicate with the blood sampling side port 40. The piston 14 has been advanced proximally for purposes of drawing the first obtained fluid 70 considered too dilute for laboratory testing into the fluid chamber 36 as shown in FIG. 1. A substantially minimal amount of first obtained fluid 70 is drawn into the inner cannula 28 having a substantially narrow inner diameter defined by an inner wall 78. The second obtained fluid 66 is now at rest at the distal hub opening 32.

Figure 5:
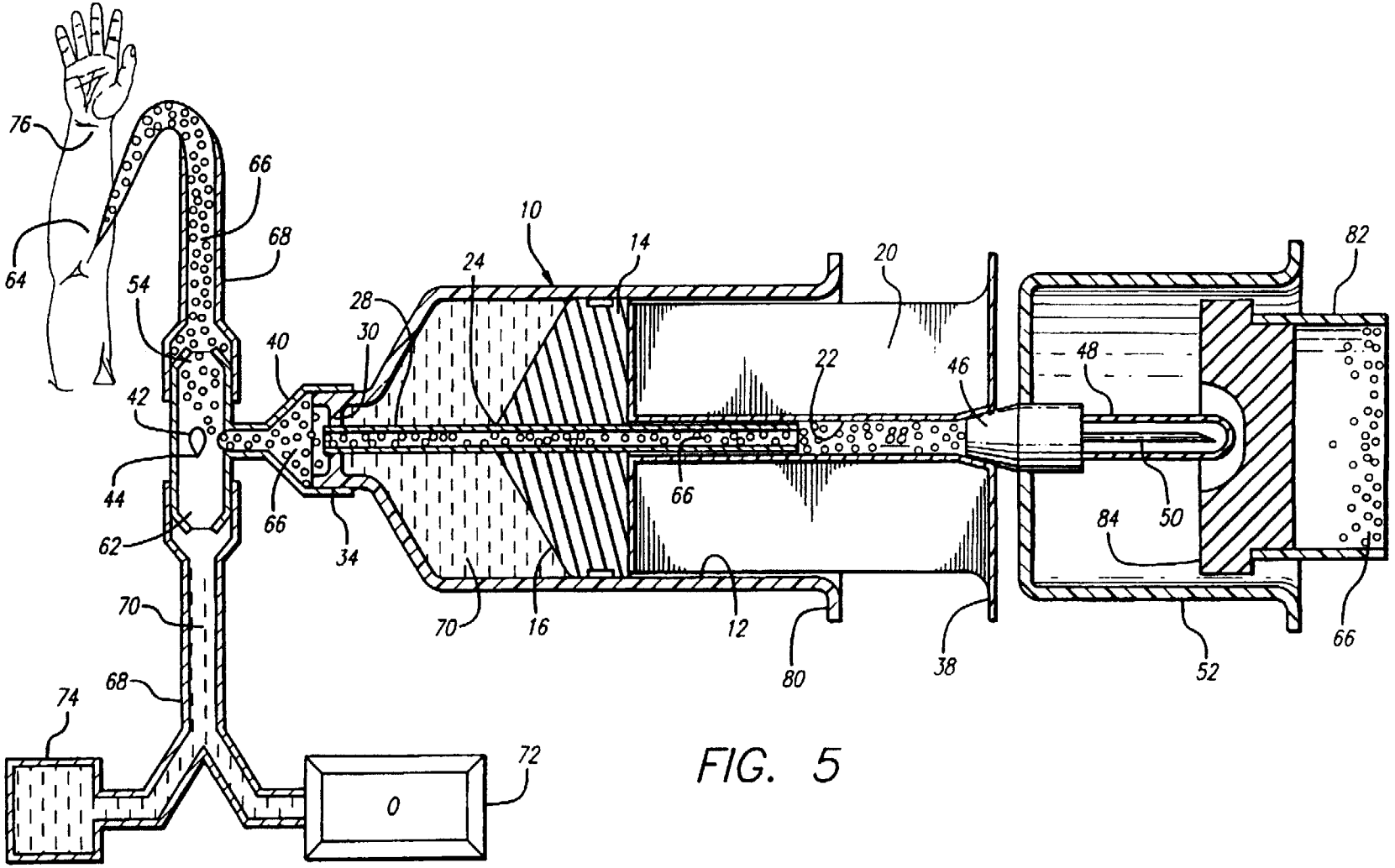
FIG. 5 is a sectional view of the syringe of the present invention showing a second obtained fluid within the inner cannula, the plunger-conduit system and a vacuum glass tube.

FIG. 5 shows the second obtained fluid 66 considered appropriate for laboratory testing having passed through the inner cannula 28, the conduit 22 of the plunger 20 and into a vacuum glass tube 82 having a rubber plug 84 when the needle 48 is caused to penetrate the rubber plug 84. The first obtained fluid 70 remains substantially separate from the second obtained fluid 66 when the vacuum glass tube 82 is inserted into the proximal end of the blood collection receptacle 52.

Figure 6:
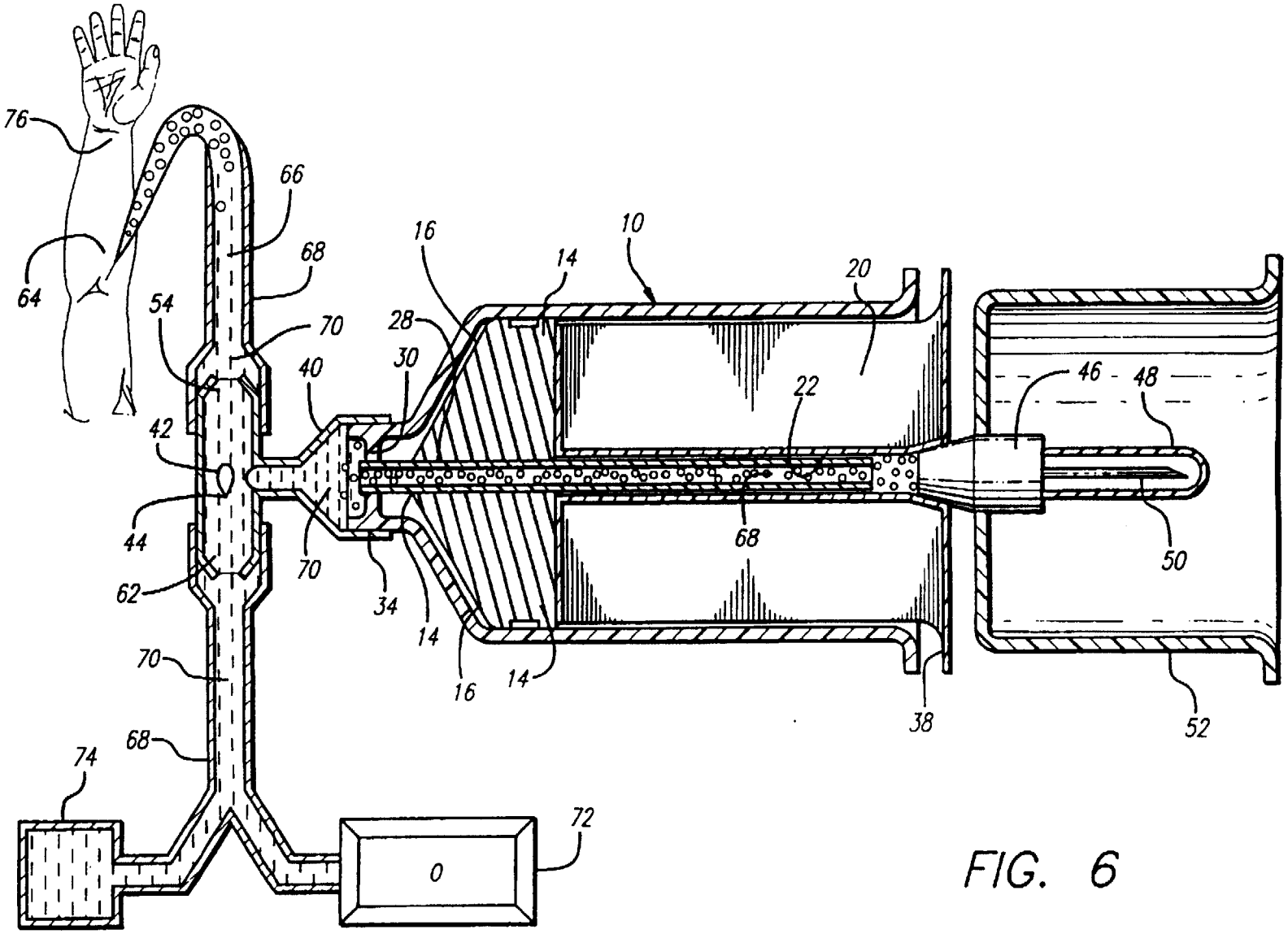
FIG. 6 is a sectional view of the syringe of the present invention showing the first obtained fluid having been returned to the patient.

FIG. 6 shows the first obtained fluid 70 considered too dilute for laboratory testing having been returned to the patient's radial artery.

Figure 7:
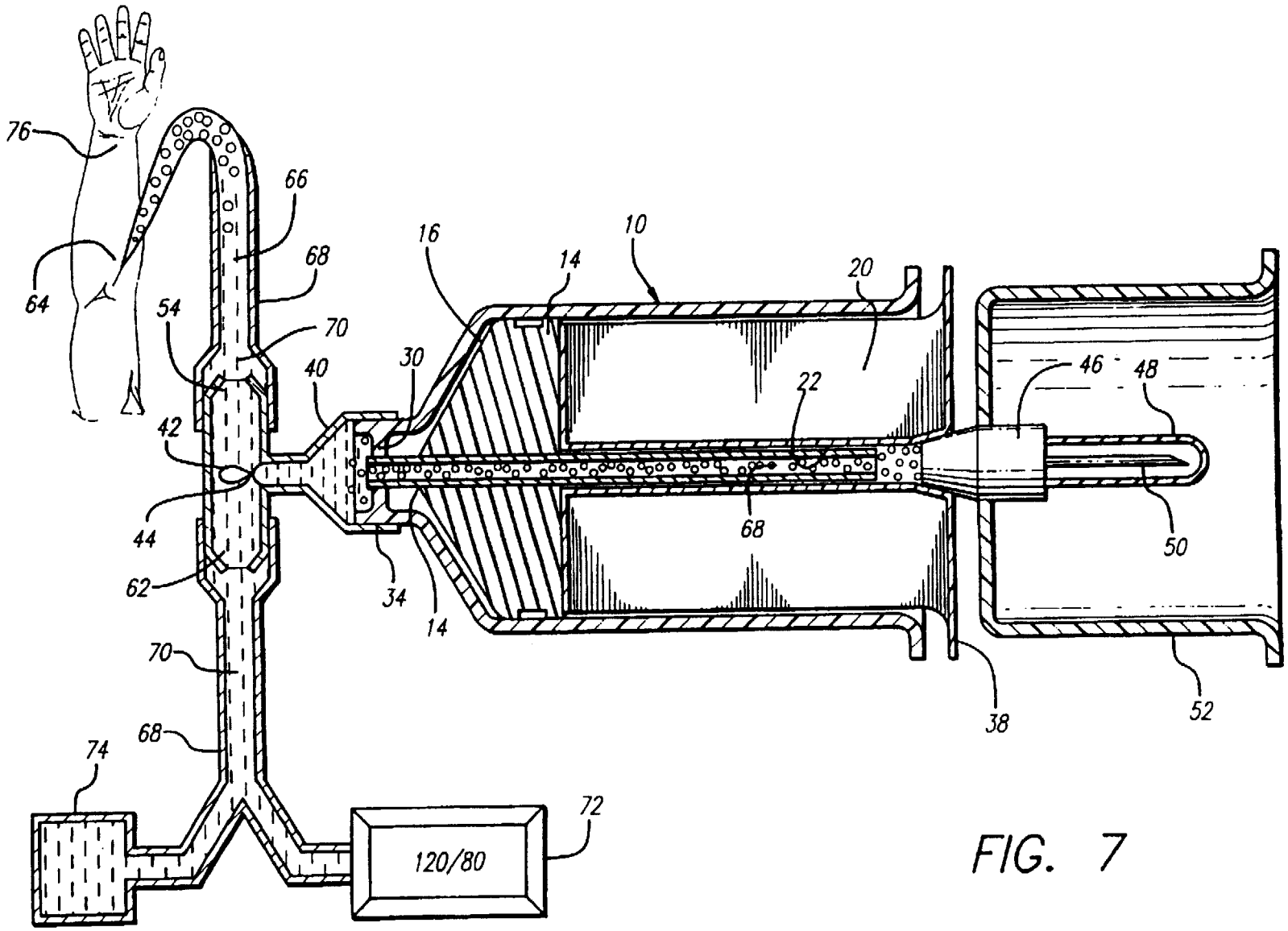
FIG. 7 is a sectional view of the syringe of the present invention showing the three-way valve positioned to allow continuous monitoring of a patient's blood pressure.

FIG. 7 shows the three-way valve 42 with the off indicator tip 44 directed toward the blood sampling side port 40 so as to allow the pressure transducer 72 to record the patient's blood pressure.

Figure 8:
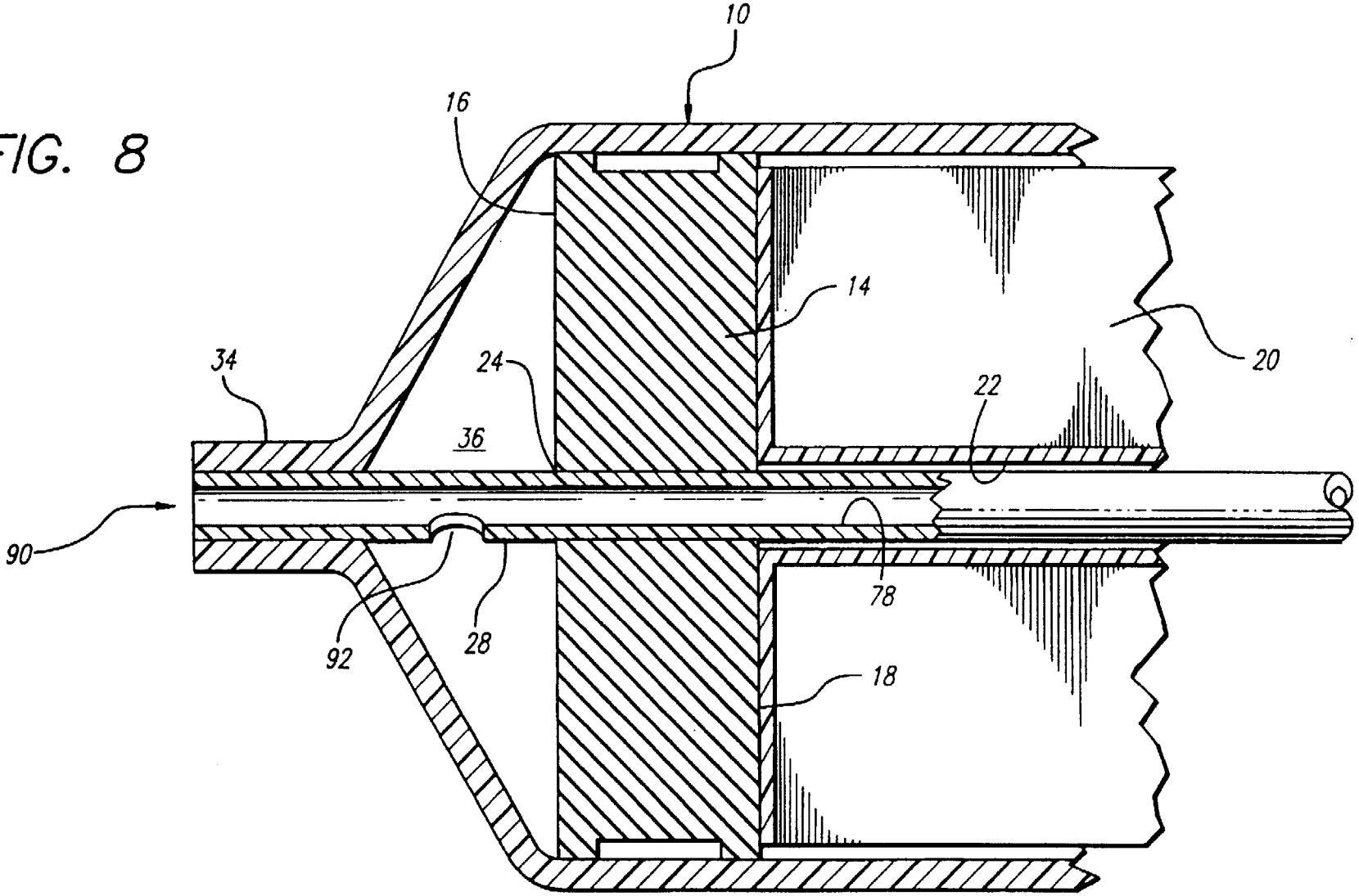
FIG. 8 is an alternate embodiment of the distal portion of the syringe of the present invention with the inner cannula having a side opening within the fluid chamber.

FIG. 8 is an exploded view of an alternative embodiment of the distal hub 34. The inner cannula 28 is integral with the distal hub 34 such that only a single distal opening 90 allows fluid to enter the fluid chamber 36 via a side opening 92 integral with the inner wall 78 of the inner cannula 28. The distinctive operative elements require manual positioning of the plunger 20 to prevent forward displacement of the piston 14 when the vacuum glass tube 82 is inserted into the proximal end of the blood collection receptacle.

It will be appreciated that the method and apparatus illustrated above enable the benefits of obtaining a plurality of blood samples from second obtained fluid to be enjoyed using a single syringe. The collection of blood samples from indwelling catheters is universally made safe, simple, efficient and cost effective. The syringe apparatus of this invention makes a traditionally cumbersome and time consuming procedure a welcomed necessity.

Having thus described the invention what I desire to claim and secure by Letters Patent is:

1. A syringe for the extraction of a fluid into at least one fluid chamber or the injection of a fluid comprising:

(a) a cylindrical body having a distal end and an open proximal end, said distal end including a partial opening and a portion of a size and shape adapted for mounting an indwelling catheter thereon, said distal end being open to the flow of a first fluid into and out of said cylindrical body through said partial opening at all times when said syringe is in use;

(b) a piston sealably engaging and slidable along the interior wall of said cylindrical body, said piston including a piston face extending transversely across said interior wall and defining a fluid chamber between said piston face and said distal end of said cylindrical body;

(c) plunger means for moving said piston proximally or distally within said cylindrical body, said plunger means being attached at one end to said piston, said plunger means having another end extending beyond said open proximal end of said cylindrical body, said plunger means having a size and shape that minimizes substantial lateral motion in said cylindrical body;

(d) extending distally and not beyond said distal end, an inner cannula having a blunt distal orifice and a blunt proximal orifice, said inner cannula further having an interior portion, said interior portion having a substantially narrow, uniform internal diameter adapted for passing a separate second fluid therethrough, said inner cannula further having an exterior portion, said inner cannula being rigidly held in said distal end by support means so as to position substantially permanent said blunt distal orifice in said partial opening, said inner cannula being integral with said support means so as to be able to allow the flow of said first fluid past said blunt distal orifice and into and out of said fluid chamber, said inner cannula further being rigidly held in said distal end by support means to assure said first fluid remains substantially separate from said interior portion, said inner cannula further being rigidly held in said distal end by support means so as to substantially prevent the flow of said first fluid through said inner cannula, said blunt distal orifice further being positioned by support means to allow mounting of said indwelling catheter on said portion; and (e) operatively disposed in relationship to said blunt proximal orifice, sealing means for preventing the retrograde flow of air into said inner cannula, said sealing means comprising a fluid collection receptacle, said fluid collection receptacle including a passage that communicates with said interior portion of said inner cannula.

2. A syringe as defined in claim 1 wherein said inner cannula, further extending proximally and centrally into said cylindrical body, further being integral with said support means so as to be able to allow the flow of said first fluid around said exterior portion of said inner cannula and into and out of said fluid chamber.

3. A syringe as defined in claim 1 wherein said piston further includes a central opening of a size and shape adapted for slidably and sealably engaging said exterior portion of said inner cannula at all times.

4. A syringe as defined in claim 1 wherein said plunger means includes conduit means extending proximally and distally through said plunger means, said conduit means including an open distal end, said conduit means further including an open proximal end being sealably engaged by said fluid collection receptacle, said conduit means having a sufficiently wide internal diameter to allow the passage of said inner cannula therethrough at all times, said conduit means further having a uniform internal diameter to induce the passage of said separate second fluid through said inner cannula and said plunger means and into said fluid collection receptacle.

5. A syringe for the extraction of a fluid into at least one fluid chamber or the injection of a fluid comprising:

(a) a cylindrical body having a distal end and an open proximal end, said distal end including a partial opening and a portion of a size and shape adapted for mounting an indwelling catheter thereon, said distal end being open to the flow of a first fluid into and out of said cylindrical body through said partial opening at all times when said syringe is in use;

(b) extending distally and not beyond said distal end, an inner cannula having a blunt distal orifice and a blunt proximal orifice, said inner cannula further having an interior portion, said interior portion having a substantially narrow, uniform internal diameter adapted for passing a second fluid therethrough, said inner cannula further having an exterior portion, said inner cannula being rigidly held in said distal end by support means so as to position substantially permanent said blunt distal orifice in said partial opening, said inner cannula being integral with said support means so as to be able to allow the flow of said first fluid past said blunt distal orifice, said inner cannula further being rigidly held in said distal end by support means to assure said first fluid remains substantially separate from said interior portion, said inner cannula further being rigidly held in said distal end by support means so as to substantially prevent the flow of said first fluid through said inner cannula, said blunt distal orifice further being positioned by support means to allow mounting of said indwelling catheter on said portion;

(c) plunger means having piston means at one end of said plunger means, said piston means sealably engaging and slidable along the interior wall of said cylindrical body, said piston means including a portion extending transversely across said interior wall and defining a fluid chamber between said piston means and said distal end of said cylindrical body, said plunger means, disposed within said cylindrical body, being adapted for moving said piston means proximally or distally so as to induce the flow of said first fluid past said blunt distal orifice and into and out of said fluid chamber, said plunger means having another end extending beyond said open proximal end of said cylindrical body, said plunger means having a size and shape that minimizes substantial lateral motion in said cylindrical body; and (d) operatively disposed in relationship to said blunt proximal orifice, sealing means for preventing the retrograde flow of air into said inner cannula, said sealing means comprising a fluid collection receptacle, said fluid collection receptacle including a passage that communicates with said interior portion of said inner cannula.

6. A syringe as defined in claim 5 wherein said inner cannula, further extending proximally and centrally throughout said cylindrical body, further being integral with said support means so as to be able to allow the flow of said first fluid around said exterior portion of said inner cannula and into and out of said fluid chamber.

7. A syringe as defined in claim 5 wherein said piston means further includes means for separating said first fluid from said second fluid, said separating means comprising a central opening having a size and shape adapted for slidably and sealably engaging said exterior portion of said inner cannula at all times.

8. A syringe as defined in claim 5 wherein said plunger means includes conduit means extending proximally and distally through said plunger means, said conduit means including an open distal end, said conduit means further including an open proximal end being sealably engaged by said fluid collection receptacle, said conduit means having a sufficiently wide internal diameter to allow the passage of said inner cannula therethrough at all times, said conduit means further having a uniform internal diameter to induce the passage of said second fluid through said inner cannula and said plunger means and into said fluid collection receptacle.

*9. A syringe for the extraction of a fluid into at least one fluid chamber or the injection of a fluid comprising:*

*(a) a cylindrical body having a distal end and an open proximal end, said distal end including an opening therethrough, said opening being adapted to allow flow of a first sample liquid into and out of said cylindrical body through said opening;*

*(b) a piston sealably engaging and slidable along an interior wall of said cylindrical body, said piston including a piston face extending transversely across said interior wall and defining a fluid chamber between said piston face and said distal end of said cylindrical body;*

*(c) a plunger attached to a proximal end of said piston, said plunger extending proximally beyond said open proximal end of said cylindrical body, said plunger being adapted to move said piston proximally or distally within said cylindrical body; and*

*(d) an inner cannula extending proximally from said distal end, and having a distal orifice and a proximal orifice, said inner cannula further having an interior channel adapted for passing a second sample liquid therethrough, said inner cannula being held in said distal end by a support therein so as to retain in position substantially permanently said distal orifice in said opening, said inner cannula being adapted to allow the flow of said first sample liquid past said distal orifice and into and out of said fluid chamber, while assuring that said first sample liquid remains substantially separate from said interior channel.*

*10. The syringe of claim 9, further comprising a fluid collection receptacle including a passage that communicates with said interior channel of said inner cannula.*

*11. A syringe for extracting an isolated sample of fluid, said syringe comprising:*

*a cylindrical body having an interior wall, an open proximal end, and a distal end, said distal end having a distal opening therethrough;*

*a plunger assembly slidably disposed in said proximal end, said plunger assembly sealably engaging said interior wall of said cylindrical body, thereby defining a fluid chamber between a distal face of said plunger assembly and said distal end of said cylindrical body; and*

*a cannula attached in said cylindrical body, and extending proximally from said distal end, said cannula having a distal orifice, said distal orifice being adapted to allow a first fluid sample to be drawn through said distal opening into said fluid chamber, said cannula having an interior channel communicating with said distal orifice allowing a second fluid sample to be drawn through said distal opening into said interior channel, while remaining substantially separate from said first fluid sample.*

*12. The syringe of claim 11, wherein said distal face of said plunger assembly includes an opening therein, and wherein said cannula extends proximally into said opening, said opening being adapted to slidably and sealably engage said cannula.*

*13. The syringe of claim 12, wherein said plunger assembly includes a conduit therein extending proximally from said opening in said distal face, said conduit being adapted to allow said second fluid sample in said cannula to pass therethrough.*

*14. The syringe of claim 13, further comprising a fluid collection receptacle on a proximal end of said plunger assembly in communication with said conduit.*

*15. The syringe of claim 13, further comprising a blood collection needle extending proximally from said conduit.*

*16. The syringe of claim 11, wherein said distal orifice of said cannula is attached to said distal end of said cylindrical body by an integral support.*

*17. The syringe of claim 11, wherein said interior channel has a substantially narrow, uniform diameter.*

*18. A syringe for extracting an isolated sample of fluid, said syringe comprising:*

*a cylindrical body having an interior wall, an open proximal end, and a distal end, said distal end having a distal opening therethrough;*

*a piston slidably disposed in said proximal end, said piston sealably engaging said interior wall of said cylindrical body, thereby defining a fluid chamber between a piston face of said piston and said distal end of said cylindrical body;*

*a plunger attached to said piston and extending proximally therefrom, said plunger being adapted to move said piston proximally and distally within said cylindrical body; and*

*a cannula attached to said distal end of said cylindrical body and extending proximally therefrom, said cannula having a cross-section smaller than a cross-section of said distal opening, thereby allowing a first fluid sample to be drawn into and out of said fluid chamber through said distal opening, said cannula having an interior channel allowing a second fluid sample to be drawn therethrough while remaining substantially separate from said first fluid sample.*

*19. The syringe of claim 18, wherein said cannula includes a distal end having a distal orifice therein, said distal orifice communicating with said interior channel, said distal orifice being located adjacent said distal opening.*

*20. The syringe of claim 19, wherein said distal end of said cannula is fixedly attached in said distal opening by a support.*

*21. The syringe of claim 18, further comprising a conduit extending proximally from an opening in said piston face through said plunger, said cannula sealably and slidably telescoping into said conduit, thereby allowing said second fluid sample to pass through said conduit.*

*22. The syringe of claim 21, further comprising a fluid collection receptacle on a proximal end of said plunger, said fluid collection receptacle sealably communicating with said conduit.*

*23. The syringe of claim 22, wherein said fluid collection receptacle includes a vacuum tube attachable to said fluid*

*collection receptacle, thereby allowing said second fluid sample to be received within said vacuum tube.*

*24. The syringe of claim 21, further comprising a blood collection needle extending proximally from a proximal end of said plunger and being sealably housed in a sleeve, said blood collection needle communicating with said conduit, said blood collection needle being adapted to detachably receive a vacuum tube thereon.*

* * * * *